(12) United States Patent
Sharonov (10) Patent No.: US 9,561,022 B2
(45) Date of Patent: Feb. 7, 2017

(54) DEVICE AND METHOD FOR OPTICAL IMAGE CORRECTION IN METROLOGY SYSTEMS

(71) Applicant: Covidien LP, Mansfield, MA (US)

(72) Inventor: Alexey Sharonov, Bethany, CT (US)

(73) Assignee: Covidien LP, Mansfield, MA (US)

(*) Notice: Subject to any disclaimer, the term of this patent is extended or adjusted under 35 U.S.C. 154(b) by 907 days.

(21) Appl. No.: 13/755,289

(22) Filed: Jan. 31, 2013

(65) Prior Publication Data

US 2013/0226156 A1 Aug. 29, 2013

Related U.S. Application Data

(60) Provisional application No. 61/603,460, filed on Feb. 27, 2012.

(51) Int. Cl.
*A61B 17/00* (2006.01)
*G01B 11/28* (2006.01)
*G01B 11/25* (2006.01)
*G02B 23/24* (2006.01)

(52) U.S. Cl.
CPC ..... *A61B 17/00234* (2013.01); *G01B 11/2531* (2013.01); *G02B 23/2461* (2013.01)

(58) Field of Classification Search
CPC ............ A61B 1/041; A61B 1/05; A61B 1/06; A61B 1/065; A61B 1/00163; A61B 1/00172; A61B 1/00174; G01B 11/02; G01B 11/028; G01B 11/03; G01B 11/08; G01B 11/016; G03F 7/70625; G03F 7/70633; G03F 7/70666
(Continued)

(56) References Cited

U.S. PATENT DOCUMENTS

| 2,788,390 A | 4/1957 | Sheldon |
| 3,817,635 A | 6/1974 | Kawahara |
| 3,819,267 A | 6/1974 | Kawahara |

(Continued)

FOREIGN PATENT DOCUMENTS

| DE | 3629435 A1 | 3/1987 |
| DE | 10 2010 025752 | 1/2012 |

(Continued)

OTHER PUBLICATIONS

European Search Report from EP 12190094.8 dated Mar. 4, 2013 (6 pgs.).

(Continued)

*Primary Examiner* — Ahmed Farah (57) ABSTRACT

An optical metrology and image correction device includes a point size light source adapted to emit a beam of light and a translucent mask that receive the beam of light. The translucent mask rotates from a first position wherein the beam of light is received by the translucent mask in a direction substantially orthogonal to the translucent mask to a second position wherein the beam of light is received by the translucent mask at an angle offset with respect to the translucent mask. A corresponding method of measuring and correcting an image from an optical metrology and image correction device includes emitting a beam of light from a point size light source, causing the beam of light to be received by a translucent mask in a first position substantially orthogonal to the mask and in a second position in a direction offset with respect to the translucent mask.

14 Claims, 6 Drawing Sheets

(58) Field of Classification Search
USPC ......... 606/1, 13–19, 130; 600/101–106, 108, 600/109, 111; 356/3, 3.01, 3.03–3.05, 356/3.09, 625, 628, 629; 128/898
See application file for complete search history.

(56) References Cited

U.S. PATENT DOCUMENTS

| | | | |
|---|---|---|---|
| 3,854,822 | A | 12/1974 | Altman et al. |
| 3,943,361 | A | 3/1976 | Miller |
| 4,281,931 | A | 8/1981 | Chikama |
| 4,660,982 | A | 4/1987 | Okada |
| 4,702,229 | A | 10/1987 | Zobel |
| 4,895,431 | A | 1/1990 | Tsujiuchi et al. |
| 4,935,810 | A | 6/1990 | Nonami et al. |
| 4,958,932 | A | 9/1990 | Kegelman et al. |
| 4,980,763 | A | 12/1990 | Lia |
| 4,986,262 | A | 1/1991 | Saito |
| 5,090,400 | A | 2/1992 | Saito |
| 5,200,838 | A | 4/1993 | Nudelman et al. |
| 5,261,404 | A | 11/1993 | Mick et al. |
| 5,381,236 | A | 1/1995 | Morgan |
| 5,428,447 | A * | 6/1995 | Toida ............... G02B 26/10 356/432 |
| 5,469,254 | A | 11/1995 | Konomura |
| 5,573,492 | A | 11/1996 | Dianna et al. |
| 5,576,975 | A | 11/1996 | Sasaki et al. |
| 5,633,675 | A | 5/1997 | Danna et al. |
| 5,669,871 | A | 9/1997 | Sakiyama |
| 5,776,050 | A | 7/1998 | Chen et al. |
| 5,801,762 | A | 9/1998 | Dianna et al. |
| 5,860,912 | A | 1/1999 | Chiba |
| 5,967,968 | A | 10/1999 | Nishioka |
| 6,009,189 | A | 12/1999 | Schaack |
| 6,063,023 | A | 5/2000 | Sakiyama |
| 6,134,003 | A | 10/2000 | Tearney et al. |
| 6,178,346 | B1 | 1/2001 | Amundson et al. |
| 6,191,862 | B1 | 2/2001 | Swanson et al. |
| 6,205,243 | B1 | 3/2001 | Migdal et al. |
| 6,263,234 | B1 | 7/2001 | Engelhardt et al. |
| 6,301,416 | B1 | 10/2001 | Okano et al. |
| 6,482,148 | B1 | 11/2002 | Luke |
| 6,503,195 | B1 | 1/2003 | Keller et al. |
| 6,508,761 | B1 | 1/2003 | Ramsbottom et al. |
| 6,520,959 | B1 * | 2/2003 | Iwahashi ............ A61N 5/0601 606/13 |
| 6,542,249 | B1 | 4/2003 | Kofman et al. |
| 6,569,088 | B2 | 5/2003 | Koshikawa |
| 6,663,560 | B2 | 12/2003 | MacAulay et al. |
| 6,750,971 | B2 | 6/2004 | Overbeck et al. |
| 6,832,985 | B2 | 12/2004 | Irion et al. |
| 6,890,296 | B2 | 5/2005 | Ogawa |
| 6,937,268 | B2 | 8/2005 | Ogawa |
| 6,945,930 | B2 | 9/2005 | Yokota |
| 7,046,376 | B2 * | 5/2006 | Sezginer ............ G01B 11/0616 356/601 |
| 7,066,930 | B2 | 6/2006 | Boll et al. |
| 7,193,713 | B2 | 3/2007 | Shiode et al. |
| 7,310,431 | B2 | 12/2007 | Gokturk et al. |
| 7,317,954 | B2 | 1/2008 | McGreevy |
| 7,317,955 | B2 | 1/2008 | McGreevy |
| 7,556,599 | B2 | 7/2009 | Rovegno |
| 7,564,626 | B2 | 7/2009 | Bendall et al. |
| 7,794,388 | B2 | 9/2010 | Draxinger et al. |
| 7,809,225 | B2 | 10/2010 | Bouma et al. |
| 7,819,798 | B2 | 10/2010 | Krauter et al. |
| 2002/0156380 | A1 | 10/2002 | Feld et al. |
| 2002/0188172 | A1 | 12/2002 | Irion et al. |
| 2003/0135101 | A1 | 7/2003 | Webler |
| 2003/0191363 | A1 | 10/2003 | Boll et al. |
| 2004/0147808 | A1 | 7/2004 | MacAulay et al. |
| 2004/0242961 | A1 * | 12/2004 | Bughici ............... A61B 1/07 600/108 |
| 2005/0085717 | A1 | 4/2005 | Shahidi |
| 2005/0090749 | A1 | 4/2005 | Rubbert |
| 2005/0124988 | A1 | 6/2005 | Terrill-Grisoni |
| 2005/0237423 | A1 | 10/2005 | Nilson et al. |
| 2005/0277186 | A1 | 12/2005 | Fein et al. |
| 2006/0044546 | A1 | 3/2006 | Lewin et al. |
| 2006/0103854 | A1 | 5/2006 | Franke et al. |
| 2006/0235273 | A1 | 10/2006 | Moriyama et al. |
| 2007/0060792 | A1 | 3/2007 | Draxinger et al. |
| 2007/0156018 | A1 | 7/2007 | Krauter et al. |
| 2007/0225550 | A1 | 9/2007 | Gattani et al. |
| 2008/0016487 | A1 * | 1/2008 | Wen .................. G03F 7/70633 430/22 |
| 2008/0024793 | A1 | 1/2008 | Gladnick |
| 2008/0068197 | A1 | 3/2008 | Neubauer et al. |
| 2008/0200808 | A1 | 8/2008 | Leidel et al. |
| 2008/0221446 | A1 | 9/2008 | Washburn et al. |
| 2008/0284979 | A1 | 11/2008 | Yee et al. |
| 2008/0285913 | A1 | 11/2008 | Yang et al. |
| 2009/0002485 | A1 | 1/2009 | Fujiwara |
| 2009/0082629 | A1 | 3/2009 | Dotan et al. |
| 2009/0103050 | A1 | 4/2009 | Michaels et al. |
| 2009/0116023 | A1 | 5/2009 | Wadman |
| 2009/0221874 | A1 | 9/2009 | Vinther et al. |
| 2009/0221922 | A1 | 9/2009 | Lec et al. |
| 2009/0270682 | A1 | 10/2009 | Visser |
| 2009/0323084 | A1 | 12/2009 | Dunn et al. |
| 2010/0036393 | A1 | 2/2010 | Unsworth |
| 2010/0201796 | A1 | 8/2010 | Chan |
| 2010/0265463 | A1 | 10/2010 | Lai |
| 2010/0280321 | A1 | 11/2010 | Modell |
| 2011/0054308 | A1 | 3/2011 | Cohen et al. |
| 2011/0279670 | A1 | 11/2011 | Park |
| 2012/0101370 | A1 | 4/2012 | Razzaque et al. |
| 2012/0293812 | A1 * | 11/2012 | Sharonov ............ A61B 5/1076 356/625 |
| 2013/0226037 | A1 * | 8/2013 | Pinto .................. A61B 5/1076 600/587 |

FOREIGN PATENT DOCUMENTS

| | | |
|---|---|---|
| EP | 0403399 A2 | 12/1990 |
| EP | 1480067 A1 | 11/2004 |
| EP | 2106748 A1 | 10/2009 |
| JP | 2011 185767 | 9/2011 |
| WO | WO 00/08415 | 2/2000 |
| WO | WO 2005/013814 | 2/2005 |

OTHER PUBLICATIONS

European Search Report from EP 12168466.6 dated Mar. 26, 2013 (10 pgs.).
European Search Report from EP 13156689.5 dated Apr. 26, 2013 (7 pgs.).
European Search Report from EP12190097.1 dated Sep. 16, 2013. (6 pgs.).
European Search Report from EP13172563.2 dated Oct. 1, 2013. (8 pgs.).
European Search Report for Application No. 13 17 7731 dated Nov. 28, 2013.
U.S. Appl. No. 13/645,559, filed Oct. 5, 2012, United States Surgical.
U.S. Appl. No. 13/650,156, filed Oct. 12, 2012, United States Surgical.
European Search Report, Application No. EP 13 17 7731 dated Mar. 24, 2014.
European Search Report for Application No. 13156676.2-1553 date of completion Jun. 24, 2013 (7 pages).

* cited by examiner

DEVICE AND METHOD FOR OPTICAL IMAGE CORRECTION IN METROLOGY SYSTEMS

CROSS REFERENCE TO RELATED APPLICATION

The present application claims the benefit of and priority to U.S. Provisional Application Ser. No. 61/603,460, filed on Feb. 27, 2012, the entire contents of which are incorporated herein by reference.

BACKGROUND

1. Technical Field

The present disclosure relates to a method for measuring a dimension of a target site. More particularly, the present disclosure relates to methods of projecting and correcting images for use in measuring a dimension of a target site.

2. Background of the Related Art

Minimally invasive surgery, e.g., laparoscopic, endoscopic, and thoroscopic surgery, has many advantages over traditional open surgeries. In particular, minimally invasive surgery eliminates the need for a large incision, thereby reducing discomfort, recovery time, and many of the deleterious side effects associated with traditional open surgery.

The minimally invasive surgeries are performed through small openings in a patient's skin. These openings may be incisions in the skin or may be naturally occurring body orifices (e.g., mouth, anus, or vagina). In general, insufflation gas is used to enlarge the area surrounding the target surgical site to create a larger, more accessible work area.

During minimally invasive procedures, it is often difficult for a surgeon to determine sizes of various organs, tissues, and other structures in a surgical site. Various in-situ surgical metrology methods exist for measurement in a surgical site. Such methods require many moving parts and projection images that change size and/or focus quickly as projectors move in or out of a surface of projection.

In-situ surgical metrology optical projection methods are employed in situations where it is desired to measure the size of defects and to correlate the size of the defects with commercially available mesh sizes for ventral hernia repair. Such methods often employ an optical projection device that includes a laser light source and diffractive optics to generate a light pattern on an area of interest. In other methods, a light source and lens system is used to project an image on the surgical site.

In projected-pattern metrology, the projected image or pattern serves as an optical ruler, where the distance between dots or lines in the pattern is directly translated to actual distances. In laparoscopic applications, when the instrument is inserted through a laparoscopic port, it is not always possible to position the projection device in front of the site to be measured. When the surface of the projection is tilted or offset with respect to the optical axis, the projected image becomes distorted, which results in significant reduction in accuracy of the measurements. Numerical methods to correct for the reduction in accuracy are not always available for the particular scenarios encountered.

SUMMARY

The embodiments of the present disclosure advance the state of the art of optical metrology and correction of images by providing a small size light emitting source (a point source) and a mask with an image that is to be projected onto a target object. If the light source is small enough, the projected image will maintain sharp edges over a wide range of distances from the projector of the light source. The projected pattern may include a circle or other well recognizable object. If the surface of the target objected is tilted with respect to the mask, significant distortion may occur. The distortion is compensated for by introducing pre-distortions of the projected image. The degree of pre-distortion is adjusted manually by visual observation of the shape of the projected image. The procedure is complete when the projected image is corrected to an image that approximates its expected shape, e.g., a circle.

In one embodiment of the present disclosure, an optical metrology and image correction device includes a point size light source adapted to emit a beam of light; and a translucent mask configured and disposed to receive the beam of light emitted from the point size light source. The translucent mask is rotatably disposed to rotate from a first position wherein the beam of light is received by the translucent mask in a direction substantially orthogonal to the translucent mask to a second position wherein the beam of light is received by the translucent mask at an angle offset with respect to the translucent mask.

In one embodiment of the present disclosure, when the beam of light is received by the translucent mask in the first position, the beam of light may create a substantially undistorted image on a surface of a target object positioned distally from the point size light source and distally from the translucent mask, and the translucent mask and the surface of the target object may be substantially parallel to one another to define a first mask and target object position.

In yet another embodiment of the present disclosure, when the beam of light is received by the translucent mask in the first position, the beam of light may create a distorted image of the substantially undistorted image on the surface of the target object, and the translucent mask and the surface of the target object may be substantially skewed with respect to one another to define a second mask and target object position.

In one embodiment of the present disclosure, when the beam of light is received by the translucent mask in the second position, the beam of light may substantially recreate the substantially undistorted image on the surface of the target object, and the translucent mask and the surface of the target object may be substantially parallel to one another and both may be skewed with respect to the beam of light to define a third mask and target position.

The translucent mask may include an internal surface configured to cause a pre-distortion in the substantially undistorted image created by the beam of light in the first position. The target object may be tissue in the body of a patient.

The embodiments of the present disclosure also include a method of measuring and correcting an image emitted from an optical metrology and image correction device that includes the steps of emitting a beam of light from a point size light source, causing the beam of light to be received by a translucent mask in a first position wherein the beam of light is received by the translucent mask in a direction substantially orthogonal to the translucent mask, and causing the beam of light to be received by the translucent mask in a second position wherein the beam of light is received by the translucent mask in a direction at an angle offset with respect to the translucent mask.

In one embodiment of the present disclosure, when the beam of light is received by the translucent mask in the first position, the method may further include the steps of positioning the translucent mask and a surface of a target object substantially parallel to one another and creating a substantially undistorted image on the surface of the target object positioned distally from the point size light source and distally from the translucent mask.

In still another embodiment of the present disclosure, when the beam of light is received by the translucent mask in the first position, the method may further include the steps of positioning the translucent mask such that the surface of the target object is in a position substantially skewed with respect to the position of the translucent mask and creating a distorted image of the substantially undistorted image on the surface of the target object.

In one embodiment of the present disclosure, when the beam of light is received by the translucent mask in the second position, the method may further include the steps of maintaining the surface of the target object in the position substantially skewed with respect to the beam of light, rotating the translucent mask to a position substantially parallel to the surface of the target object and substantially skewed with respect to the beam of light and substantially recreating the undistorted image on the surface of the target object.

In one embodiment of the present disclosure, the step of causing the beam of light to be received by the translucent mask in the second position may include orienting an internal surface in the translucent mask to cause a pre-distortion in the substantially undistorted image created by the beam of light in the first position.

In yet another embodiment of the present disclosure, the step of positioning the translucent mask and a surface of a target object substantially parallel to one another may include positioning the translucent mask and a surface of tissue in the body of a patient parallel to one another, and the step of creating a substantially undistorted image on the surface of the target object positioned distally from the point size light source and distally from the translucent mask may include creating a substantially undistorted image on the surface of the tissue in the body of a patient positioned distally from the point size light source and distally from the translucent mask.

In one embodiment of the present disclosure, the step of positioning the optical system such that the surface of the target object is in a position substantially skewed with respect to the position of the translucent mask may include positioning the optical system such that the surface of tissue in the body of a patient is in a position substantially skewed with respect to the position of the translucent mask and the step of creating a distorted image of the substantially undistorted image on the surface of the target object may include creating a distorted image of the substantially undistorted image on the surface of the tissue in the body of a patient.

In one embodiment of the present disclosure, the step of maintaining the surface of the target object in the position substantially skewed with respect to the beam of light may include maintaining the surface of the tissue in the body of a patient in the position substantially skewed with respect to the beam of light, the step of rotating the translucent mask to a position substantially parallel to the surface of the target object and substantially skewed with respect to the beam of light may include rotating the translucent mask to a position substantially parallel to the surface of the tissue in the body of a patient and substantially skewed with respect to the beam of light, and the step of substantially recreating the undistorted image on the surface of the target object may include substantially recreating the undistorted image on the surface of the tissue in the body of a patient.

BRIEF DESCRIPTION OF THE DRAWINGS

Various embodiments will be described herein below with reference to the drawings wherein.

DETAILED DESCRIPTION

The embodiments of an optical metrology and image correction system according to the present disclosure yield methods for real-time in-body-cavity metrology employing visible, ultraviolet or near-infrared (IR) radiation, which is either coherent or incoherent, to reduce overall surgery time and the cognitive burden on the surgeon. The embodiments also potentially improve patient outcome with more accurate, smaller (depending on the miniaturization scale) incision procedures, which are less prone to human errors or miscalculations.

Improvements in the surgical procedures originate from both savings in time and from more accurate surgical choices by a given surgeon when attempting to choose measurement-dependent devices for a give in-body task or procedure, such as mesh size during a hernia repair.

Reference will now be made to the drawings, wherein like reference numerals refer to like parts.

Figure 1A:
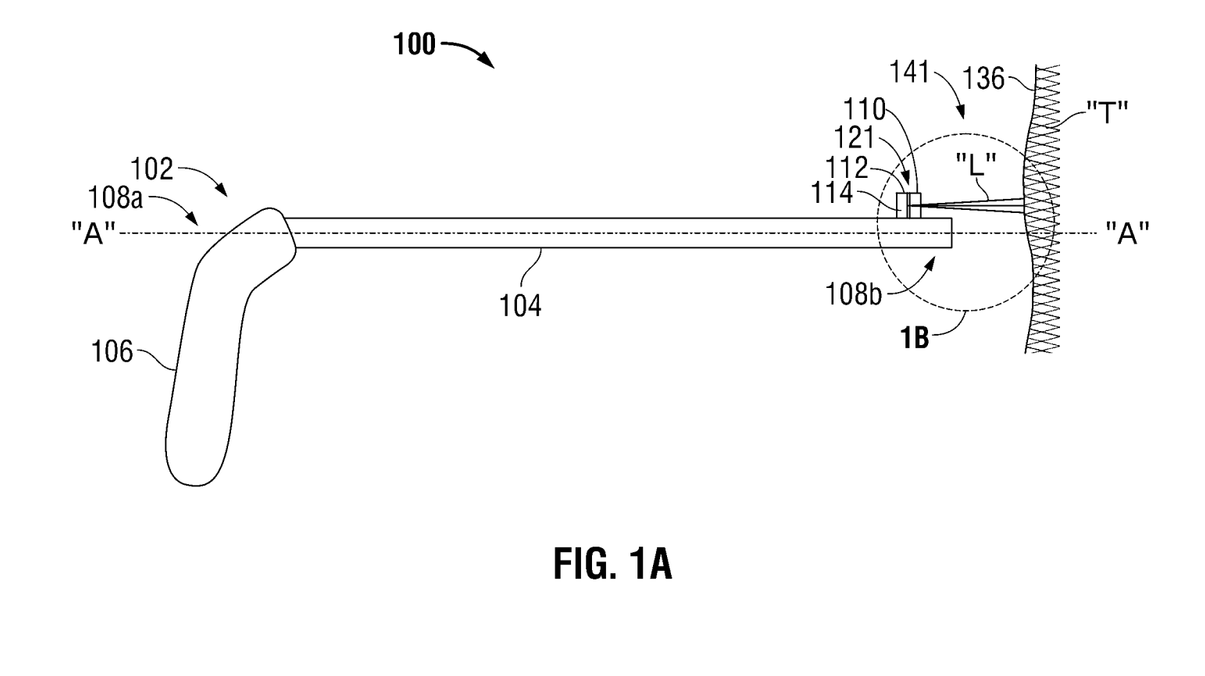
FIG. 1A is a partially schematic view of an image positioning apparatus that includes an optical metrology and image correction device according to one embodiment of the present disclosure in a first position wherein a beam of light is received by a translucent mask in a direction substantially orthogonal to the translucent mask and in a first mask and target object position creating an undistorted image.
Figure 1B:
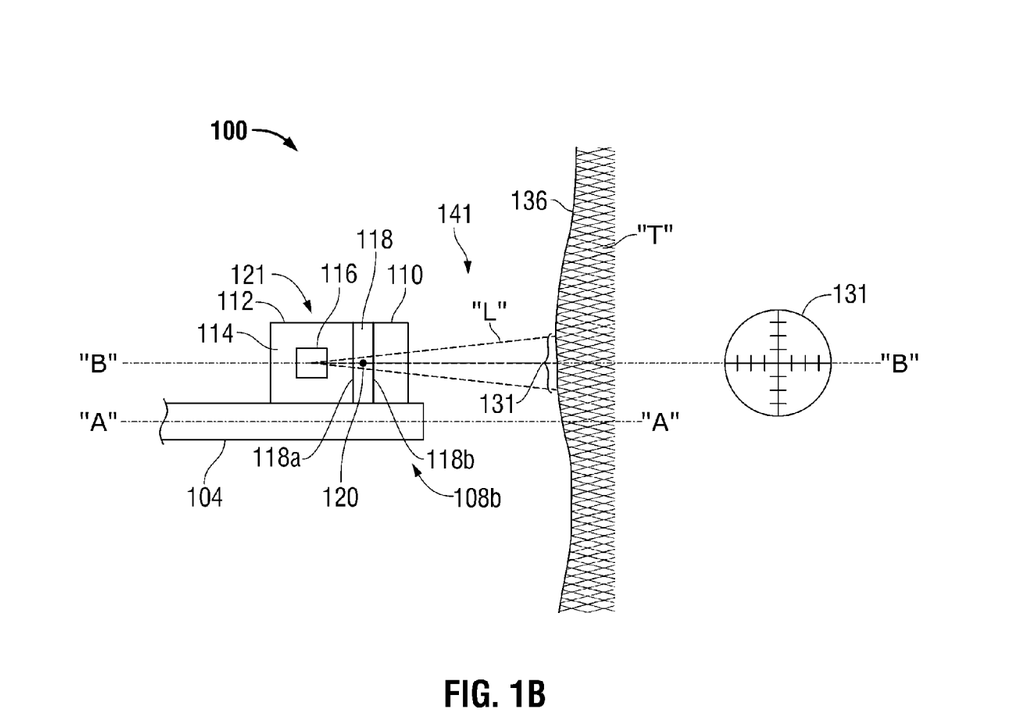
FIG. 1B is a detailed view of the optical metrology and image correction device of FIG. 1A.

Turning now to FIG. 1A and FIG. 1B, there is disclosed an image positioning apparatus 100 that includes an instrument 102. Instrument 102 includes a proximal end 108a and a distal end 108b. The instrument 102 includes an operating handle 106 at proximal end 108a and a longitudinal shaft 104 extends distally from the operating handle 106 towards distal end 108b to define a central longitudinal shaft axis "A". Although the instrument 102 may be a general purpose instrument for allowing contact with an object remotely by a user of the instrument, the instrument 102 can include a laparoscopic surgical instrument such as a stapler and is therefore shown generically.

The image positioning apparatus 100 further includes an optical metrology and image correction device 110 positioned on, and movably or immovably connected to, the shaft 104 in proximity to the distal end 108b.

The optical metrology and image correction device 110 includes a housing 112 having an interior region 114 in which is disposed a point size light source 116 that is adapted to emit a beam of light "L" in a direction generally parallel to the axis "A" to define an illumination axis "B". The device 110 further includes a translucent mask 118 that is configured and disposed to receive the beam of light "L" emitted from the point size light source 116. The translucent mask 118, which is substantially planar and defines a proximal planar surface 118a and a distal planar surface 118b, is rotatably disposed within the housing 112 to pivot around pivot point 120 so as to be capable of rotating from a first position 121 wherein the beam of light "L" is received by the translucent mask 118 in a direction substantially orthogonal to the translucent mask 118. That is, the centerline of the beam of light "L" defines the illumination axis "B" and in the first position 121, the beam of light "L" is generally orthogonal to the proximal planar surface 118a of the translucent mask 118.

As used herein, the point size light source 116 is referred to generically to represent different light sources such as lasers or laser diodes. With appropriate optics fibers, light emitting diodes (LEDs), or lasers can be utilized as point sources.

The light beam "L" may be a laser emitted by a laser diode disposed within the point source or light projector. The light beam may be emitted by an LED disposed within the point source projector. The light beam may be focused to the point by a lens disposed within the point source projector. The semi-transparent or translucent mask 118 may be translatable to adjust the magnification factor. The semi-transparent mask may be disposed within the point source projector. The point source projector may be attached to an endoscope for visually inspecting the target site. The mask pattern may include a series of uniformly spaced concentric circles. The mask pattern 131 includes a series of uniformly spaced linear markings as in the projected image 131 in FIG. 1B. In one embodiment of a point size light source, a laser may be coupled to a ball lens.

Those skilled in the art will recognize that the semi-transparent or translucent mask 118 can be custom designed and built to be suitable for the imaging described in the present disclosure. One example of a manufacturer with such capabilites is Applied Image Inc. www.appliedimage-.com, 1653 East Main Street, Rochester, N.Y. 14609 USA.

The beam of light "L" passes through the translucent mask 118 to impinge upon a target object "T", which may be patient tissue, to project a first image 131 on surface 136 of the target object "T". The translucent mask 118, and more particularly the distal surface 118b, and the surface of the target object 136 at the location of the first image 131 are substantially parallel to one another to define a first mask and target object position 141.

In the first mask and target object position 141, the beam of light "L" creates a substantially undistorted image, i.e., first image 131, on the surface 136 of the target object "T" that is positioned distally from the point size light source 116 and distally from the translucent mask 118. For illustration purposes, the first image 131, which appears on the surface 136, is illustrated as a circle projected along the illumination axis "B" to the right of the surface 136.

Figure 2A:
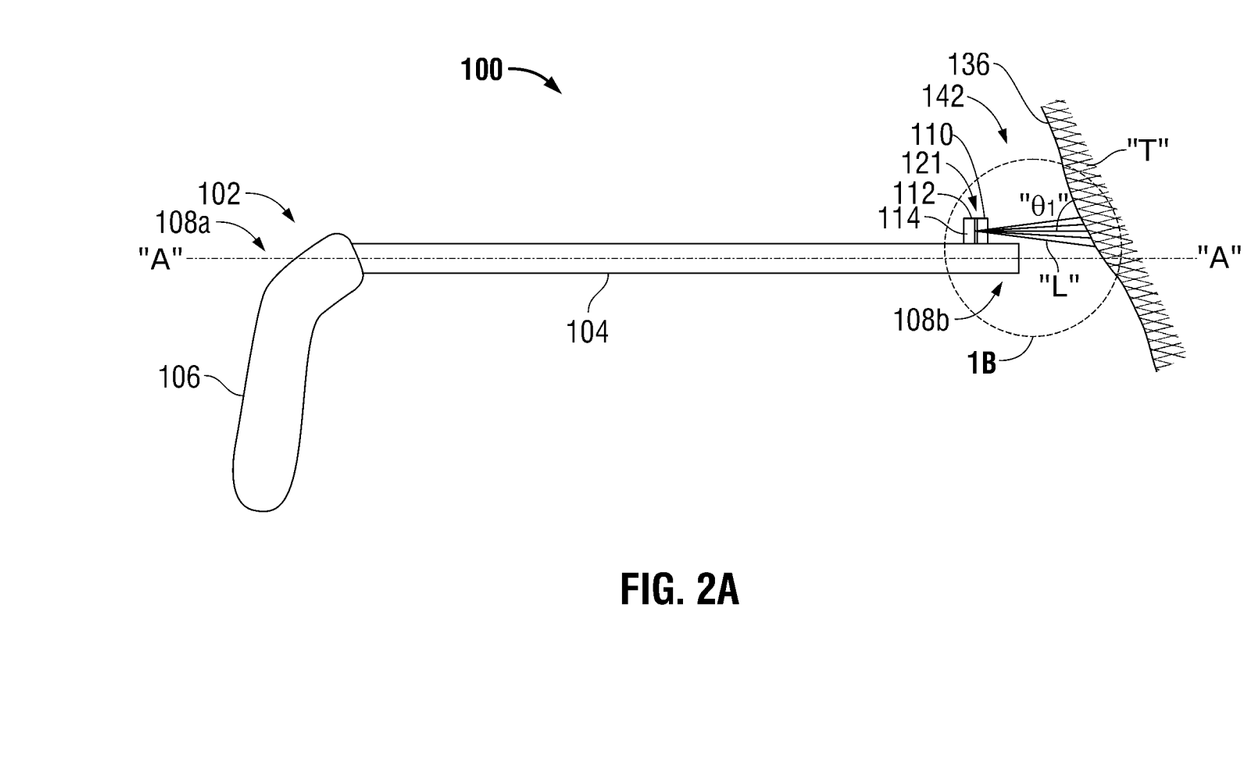
FIG. 2A is a partially schematic view of the image positioning apparatus that includes the optical metrology and image correction device of FIGS. 1A and 1B in a second mask and target object position wherein the translucent mask and the surface of the target object are substantially skewed with respect to one another creating a distorted image.
Figure 2B:
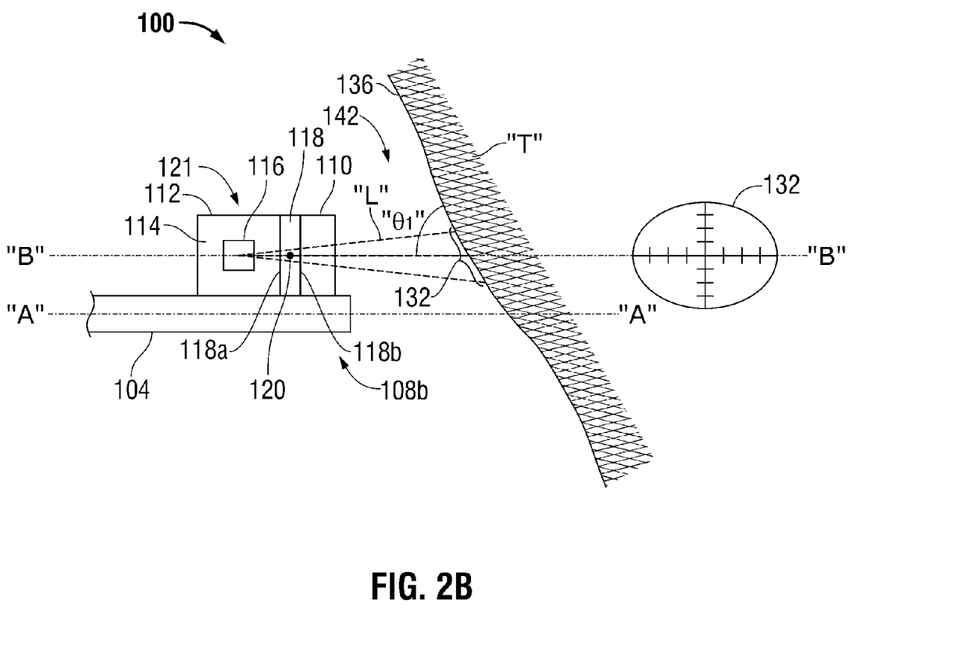
FIG. 2B is a detailed view of the optical metrology and image correction device of FIG. 2A.

FIG. 2A and FIG. 2B illustrate the image positioning apparatus 100 again in the first position 121 wherein the beam of light "L" is generally orthogonal to the proximal planar surface 118a of the translucent mask 118.

However, the optical metrology and image correction device 110 of the image positioning apparatus 100 as illustrated in FIG. 2A and FIG. 2B differs from the optical metrology and image correction device 110 of the image positioning apparatus 100 as illustrated in FIGS. 1A and 1B in that in FIGS. 2A and 2B, the surface 136 of the target object "T" is substantially skewed with respect to the translucent mask 118, and more particularly, substantially skewed with respect to the distal surface 118b of the translucent mask 118, to define a second mask and target object position 142. In the second mask and target object position 142, the beam of light "L" is received by the target object "T" at an angle "θ1" defined between the illumination axis "B" and the surface 136 of the target object "T" such that the surface 136 of the target object "T" is substantially skewed with respect to the translucent mask 118.

In the second mask and target object position 142, the beam of light "L" creates a distorted image 132 of the substantially undistorted image 131 of FIGS. 1A and 1B on the surface 136 of the target object "T". In a similar manner as described above with respect to FIGS. 1A and 1B, for illustration purposes, the second image 132, which appears on the surface 136, is illustrated as an ellipse, i.e., a distorted image of the circle or first image 131, that is again projected, for the sake of illustration, along the illumination axis "B" to the right of the surface 136.

The translucent mask 136 includes an internal surface (not specifically illustrated or numbered) that is configured to cause a pre-distortion in the substantially undistorted image 131 created by the beam of light "L" in the first position 121.

Figure 3A:
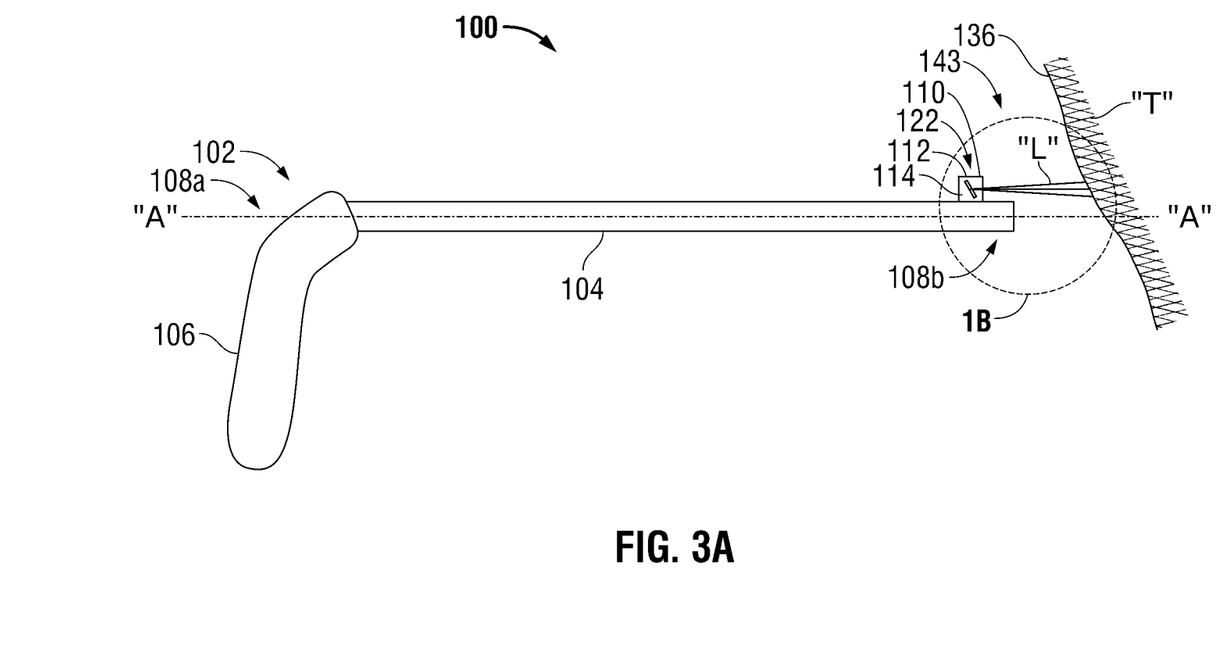
FIG. 3A is a partially schematic view of image positioning apparatus that includes the optical metrology and image correction system of FIGS. 1A, 1B and 2A, 2B in a second position wherein the beam of light is received by the translucent mask at an angle offset with respect to the translucent mask and wherein the translucent mask and the surface of the target object are substantially parallel to one another and skewed in a third mask and target position that corrects the distorted image back to an undistorted image.
Figure 3B:
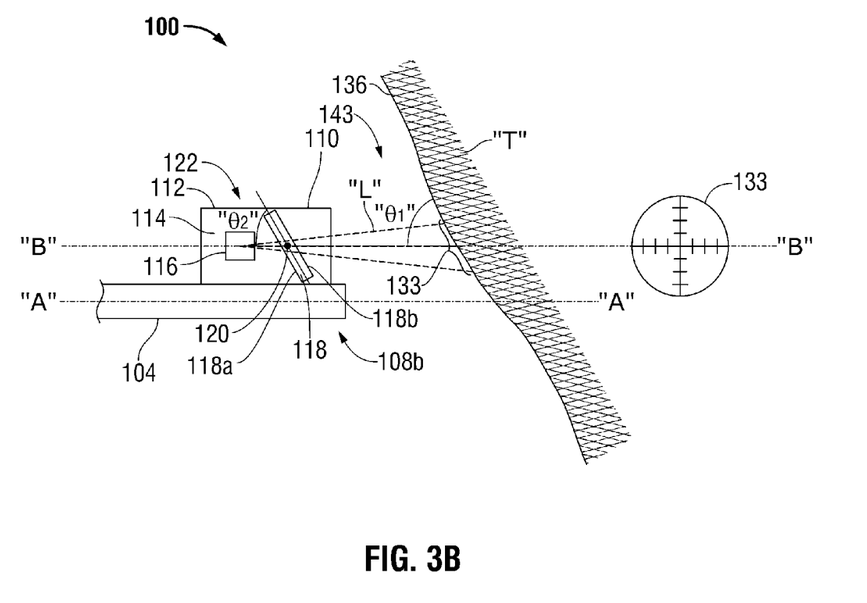
FIG. 3B is a detailed view of the optical metrology and image correction device of FIG. 3A.

FIG. 3A and FIG. 3B illustrate the optical metrology and image correction device 110 of the image positioning apparatus 100 now in a second position 122 wherein the beam of light "L" is received by the translucent mask 118 at an angle "θ2" defined between the illumination axis "B" and the translucent mask 118 that is offset with respect to the proximal planar surface 118a of the translucent mask 118. Additionally, the translucent mask 118 and the surface of the target object 136 are substantially parallel to one another and both are skewed with respect to the beam of light "L" to define a third mask and target position 143.

When the beam of light "L" is received by the translucent mask 118 in the second position 122, and when the translucent mask 118 and the surface of the target object 136 are substantially parallel to one another and both are skewed with respect to the beam of light "L" in the third mask and target position 143, the beam of light "L" substantially recreates on the surface 136 of the target object "T", as a substantially undistorted third image 133, the substantially undistorted image or first image 131 of FIGS. 1A and 1B. In a similar manner as described above with respect to FIGS. 1A and 1B and FIGS. 2A and 2B, for illustration purposes, the third image 133, which appears on the surface 136, is illustrated as a circle, i.e., a recreated undistorted image of the circle or first image 131, that is again projected along the illumination axis "B" to the right of the surface 136.

Since the translucent mask 118 and the surface of the target object 136 are substantially parallel to one another and both are skewed with respect to the beam of light "L", the angle "θ1" defined between the illumination axis "B" and the surface 136 of the target object "T" and the angle "θ2" defined between the illumination axis "B" and the translucent mask 118 are substantially equal to one another.

As indicated above, the target object "T" may be tissue or, in some cases, an organ, in the body of a patient.

Those skilled in the art will recognize that the description of FIGS. 1A, 1B, 2A, 2B, 3A, 3B also discloses in one embodiment of the present disclosure a method of measuring and correcting an image emitted from an optical metrology and image correction device, e.g., optical metrology and image correction device 110. More particularly, the method includes the steps of emitting the beam of light "L" from the point size light source 116, causing the beam of light "L" to be received by the translucent mask 118 in the first position 121 wherein the beam of light "L" is received by the translucent mask 118 in a direction substantially orthogonal to the translucent mask 118, and causing the beam of light "L" to be received by the translucent mask 118 in the second position 122 wherein the beam of light "L" is received by the translucent mask 118 in a direction such that angle "θ2", defined between the illumination axis "B" and the translucent mask 118, is offset with respect to the translucent mask 118.

When the beam of light "L" is received by the translucent mask 118 in the first position 121, the method may also include the steps of positioning the translucent mask 118 and the surface 136 of the target object "T" substantially parallel to one another and creating substantially undistorted image 131 on the surface 136 of the target object "T" that is positioned distally from the point size light source 116 and distally from the translucent mask 118.

When the beam of light "L" is received by the translucent mask 118 in the first position 121, the method may further include the steps of positioning the translucent mask 118 such that the surface 136 of the target object "T" is in a position substantially skewed with respect to the position of the translucent mask 118, e.g., as illustrated by angle "θ1" (see FIGS. 2A and 2B), and creating a distorted image, e.g., distorted image 132, of the substantially undistorted image 131 on the surface 136 of the target object "T".

When the beam of light "L" is received by the translucent mask 118 in the second position 122, the method may further includes the steps of maintaining the surface 136 of the target object "T" in the position substantially skewed with respect to the beam of light "L", e.g., as illustrated by angle "θ1" (see FIGS. 3A and 3B), and rotating the translucent mask 118 to a position substantially parallel to the surface 136 of the target object "T" and substantially skewed with respect to the beam of light "L", e.g., as illustrated by angle "θ2" (see FIGS. 3A and 3B), and substantially recreating the undistorted first image 131 of FIGS. 1A and 1B on the surface 136 of the target object "T" as undistorted third image 133.

The step of causing the beam of light "L" to be received by the translucent mask 118 in the second position 122 may include orienting the internal surface (not shown but described above) in the translucent mask 118 to cause a pre-distortion in the substantially undistorted image 131 created by the beam of light "L" in the first mask and target position 141, as illustrated by distorted image 132 in the second mask and target position 142 in FIGS. 2A and 2B.

The step of positioning the translucent mask 118 and the surface 136 of the target object "T" substantially parallel to one another may include positioning the translucent mask 118 and the surface of tissue in the body of a patient parallel to one another. Similarly, the step of creating the substantially undistorted image 131 on the surface 136 of the target object "T" positioned distally from the point size light source 116 and distally from the translucent mask 118 may include creating the substantially undistorted image 131 on the surface 136 of the tissue in the body of a patient positioned distally from the point size light source 116 and distally from the translucent mask 118.

The step of positioning the optical system 100 such that the surface 136 of the target object "T" is in a position substantially skewed with respect to the position of the translucent mask 118 includes positioning the optical system 100 such that the surface of tissue in the body of a patient is in a position substantially skewed with respect to the position of the translucent mask 118. Similarly, the step of creating the distorted image 132 of the substantially undistorted image 131 on the surface 136 of the target object "T" includes creating the distorted image 132 of the substantially undistorted image 131 on the surface of the tissue in the body of a patient.

The step of maintaining the surface 136 of the target object "T" in the position substantially skewed with respect to the beam of light "L", e.g., as illustrated by angle "θ1" in FIGS. 2A, 2B and 3A, 3B, may include maintaining the surface of the tissue in the body of a patient in the position substantially skewed with respect to the beam of light "L". The step of rotating the translucent mask 118 to a position substantially parallel to the surface 136 of the target object "T" and substantially skewed with respect to the beam of light "L" includes rotating the translucent mask 118 to a position substantially parallel to the surface of the tissue in the body of a patient and substantially skewed with respect to the beam of light"L", e.g., as illustrated by angle "θ1" in FIGS. 2A, 2B and 3A, 3B and as illustrated by angle "θ2" in FIGS. 3A, 3B. Additionally, the step of substantially recreating the undistorted image 131 on the surface 136 of the target object "T", e.g., as third image 133 in FIG. 3A, 3B, includes substantially recreating the undistorted image 131 as recreated image 133 on the surface of the tissue in the body of a patient.

As can be appreciated from the foregoing description and drawings, embodiments of an optical metrology and image correction system according to the present disclosure have been described which yield methods for real-time in-body-cavity metrology employing visible, ultraviolet or near-infrared (IR) radiation, which is either coherent or incoherent, to reduce overall surgery time and the cognitive burden on the surgeon. The embodiments also potentially improve patient outcome with more accurate, smaller (depending on the miniaturization scale) incision procedures, which are less prone to human errors or miscalculations.

Improvements in the surgical procedures originate from both savings in time and from more accurate surgical choices by a given surgeon when attempting to choose measurement-dependent devices for a give in-body task or procedure, such as mesh size during a hernia repair.

While several embodiments of the disclosure have been shown in the drawings, it is not intended that the disclosure be limited thereto, as it is intended that the disclosures be as broad in scope as the art will allow and that the specification be read likewise. Therefore, the above description should not be construed as limiting, but merely as exemplifications of particular embodiments.

What is claimed is:

1. An optical metrology and image correction device comprising:
   a point size light source adapted to emit a beam of light; and
   a translucent mask configured and disposed to receive the beam of light emitted from the point size light source, the translucent mask rotatably disposed to rotate from a first position wherein the beam of light is received by the translucent mask in a direction orthogonal to the translucent mask to a second position wherein the beam of light is received by the translucent mask at an angle offset with respect to the translucent mask, wherein when the beam of light is received by the translucent mask in the first position, the beam of light creates an undistorted image on a surface of a target object positioned distally from the point size light source and distally from the translucent mask, and wherein the translucent mask and the surface of the target object are parallel to one another to define a first mask and target object position.

2. The device according to claim 1, wherein when the beam of light is received by the translucent mask in the first position, the beam of light creates a distorted image of the undistorted image on the surface of the target object, and wherein the translucent mask and the surface of the target object are skewed with respect to one another to define a second mask and target object position.

3. The device according to claim 2, wherein when the beam of light is received by the translucent mask in the second position, the beam of light recreates the undistorted image on the surface of the target object, and wherein the translucent mask and the surface of the target object are parallel to one another and both are skewed with respect to the beam of light to define a third mask and target position.

4. The device according to claim 2, wherein the target object is tissue in the body of a patient.

5. The device according to claim 3, wherein the target object is tissue in the body of a patient.

6. The device according to claim 1, wherein the translucent mask includes an internal surface configured to cause a pre-distortion in an undistorted image created by the beam of light in the first position.

7. The device according to claim 1, wherein the target object is tissue in the body of a patient.

8. A method of measuring and correcting an image emitted from an optical metrology and image correction device comprising the steps of:

emitting a beam of light from a point size light source;

causing the beam of light to be received by a translucent mask in a first position wherein the beam of light is received by the translucent mask in a direction orthogonal to the translucent mask; and causing the beam of light to be received by the translucent mask in a second position wherein the beam of light is received by the translucent mask in a direction at an angle offset with respect to the translucent mask, wherein when the beam of light is received by the translucent mask in the first position, the method further comprises the steps of:

positioning the translucent mask and a surface of a target object parallel to one another; and creating an undistorted image on the surface of the target object positioned distally from the point size light source and distally from the translucent mask.

9. The method according to claim 8, wherein when the beam of light is received by the translucent mask in the first position, the method further comprises the steps of:

positioning the translucent mask such that the surface of the target object is in a position skewed with respect to the position of the translucent mask; and creating a distorted image of the undistorted image on the surface of the target object.

10. The method according to claim 9, wherein when the beam of light is received by the translucent mask in the second position, the method further comprises the steps of:

maintaining the surface of the target object in the position skewed with respect to the beam of light;

rotating the translucent mask to a position parallel to the surface of the target object and skewed with respect to the beam of light; and recreating the undistorted image on the surface of the target object.

11. The method according to claim 10, wherein the step of maintaining the surface of the target object in the position skewed with respect to the beam of light includes maintaining the surface of the tissue in the body of a patient in the position skewed with respect to the beam of light, wherein the step of rotating the translucent mask to a position parallel to the surface of the target object and skewed with respect to the beam of light includes rotating the translucent mask to a position parallel to the surface of the tissue in the body of a patient and skewed with respect to the beam of light, and wherein the step of recreating the undistorted image on the surface of the target object includes recreating the undistorted image on the surface of the tissue in the body of a patient.

12. The method according to claim 9, wherein the step of positioning the translucent mask such that the surface of the target object is in a position skewed with respect to the position of the translucent mask includes positioning the translucent mask such that the surface of tissue in the body of a patient is in a position skewed with respect to the position of the translucent mask, and wherein the step of creating a distorted image of the undistorted image on the surface of the target object includes creating a distorted image of the undistorted image on the surface of the tissue in the body of a patient.

13. The method according to claim 8, wherein the step of causing the beam of light to be received by the translucent mask in the second position includes orienting an internal surface in the translucent mask to cause a pre-distortion in an undistorted image created by the beam of light in the first position.

14. The method according to claim 8, wherein the step of positioning the translucent mask and a surface of a target object parallel to one another includes positioning the translucent mask and a surface of tissue in the body of a patient parallel to one another, and wherein the step of creating an undistorted image on the surface of the target object positioned distally from the point size light source and distally from the translucent mask includes creating an undistorted image on the surface of the tissue in the body of a patient positioned distally from the point size light source and distally from the translucent mask.

* * * * *